(12) United States Patent
Lerchen et al.

(10) Patent No.: US 6,506,734 B1
(45) Date of Patent: Jan. 14, 2003

(54) 20(S) CAMPTOTHECIN GLYCOCONJUGATES

(75) Inventors: Hans-Georg Lerchen; Karsten von dem Bruch, both of Leverkusen; Jörg Baumgarten; Michael Sperzel, both of Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/403,872

(22) PCT Filed: May 4, 1998

(86) PCT No.: PCT/EP98/02620
§ 371 (c)(1),
(2), (4) Date: Oct. 27, 1999

(87) PCT Pub. No.: WO98/51703
PCT Pub. Date: Nov. 19, 1998

(30) Foreign Application Priority Data

| May 14, 1997 | (DE) | 197 20 043 |
| Aug. 28, 1997 | (DE) | 197 37 477 |
| Jan. 14, 1998 | (DE) | 198 01 037 |
| Mar. 25, 1998 | (DE) | 198 13 137 |

(51) Int. Cl.⁷ ............ A61K 31/7028; C08B 15/18; C07D 491/22

(52) U.S. Cl. ............ 514/25; 514/27; 514/32; 514/34; 514/81; 514/283; 536/17.2; 536/17.3; 536/17.4; 546/23; 546/48

(58) Field of Search ............ 514/25, 27, 32, 514/34, 81, 283; 546/23, 48; 536/17.2–17.4

(56) References Cited

U.S. PATENT DOCUMENTS

| 4,604,463 A | 8/1986 | Miyasaka et al. ........ 544/125 |
| 4,943,579 A | 7/1990 | Vishnuvajjala et al. ... 514/283 |
| 5,004,758 A | 4/1991 | Boehm et al. ........... 514/283 |
| 5,496,830 A | 3/1996 | Shapiro et al. ......... 514/283 |
| 5,646,159 A | 7/1997 | Wall et al. ............ 514/279 |
| 5,773,522 A | 6/1998 | Angelucci et al. ...... 525/329.4 |
| 5,889,017 A | 3/1999 | Giovanella et al. ..... 514/283 |

FOREIGN PATENT DOCUMENTS

| DE | 42 36 237 | * 4/1994 | |
| EP | 0 418 099 | * 9/1990 | |
| EP | 0501250 | 9/1992 | C07K/9/00 |
| EP | 0 624 377 | * 5/1994 | |
| EP | 0 640 622 | * 3/1995 | |
| EP | 0 757 049 | * 2/1997 | |
| EP | 0 781 781 | * 7/1997 | |
| JP | 1246287 | 2/1989 | C07D/491/22 |
| JP | 5279370 | 10/1993 | C07D/491/22 |
| WO | 95/10304 | * 4/1995 | |
| WO | 9602546 | 2/1996 | C07D/491/22 |
| WO | 96/03152 | * 2/1996 | |
| WO | 96/26950 | * 9/1996 | |
| WO | 96/31532 | * 10/1996 | |
| WO | 9814459 | 4/1998 | C07H/17/00 |
| WO | 9815573 | 4/1998 | C07K/9/00 |

OTHER PUBLICATIONS

Yaegashi et al., "Chemical Modification of an Antitumor Alkaloid, 20(S)–Camptothecin: Glycosides, Phosphates and Sulfates of 7–ethyl–10–hydroxycamptothecin", Chem. Pharm. Bull., vol. 40(1): 131–135, Jan. 1992.*

(List continued on next page.)

Primary Examiner—Kathleen Kahler Fonda
Assistant Examiner—Leigh C. Maier
(74) Attorney, Agent, or Firm—Jerrie L. Chiu

(57) ABSTRACT

The present invention relates to glycoconjugates of 20(S)-camptothecin, in which a 3-O-methylated β-L-fucose unit is linked to the 20-hydroxyl group of a camptothecin derivative via a thiourea-modified peptide spacer. The invention furthermore relates to processes for the preparation of the compounds according to the invention and to their use as medicaments, in particular in connection with oncoses.

12 Claims, 1 Drawing Sheet

OTHER PUBLICATIONS

Figure 1:
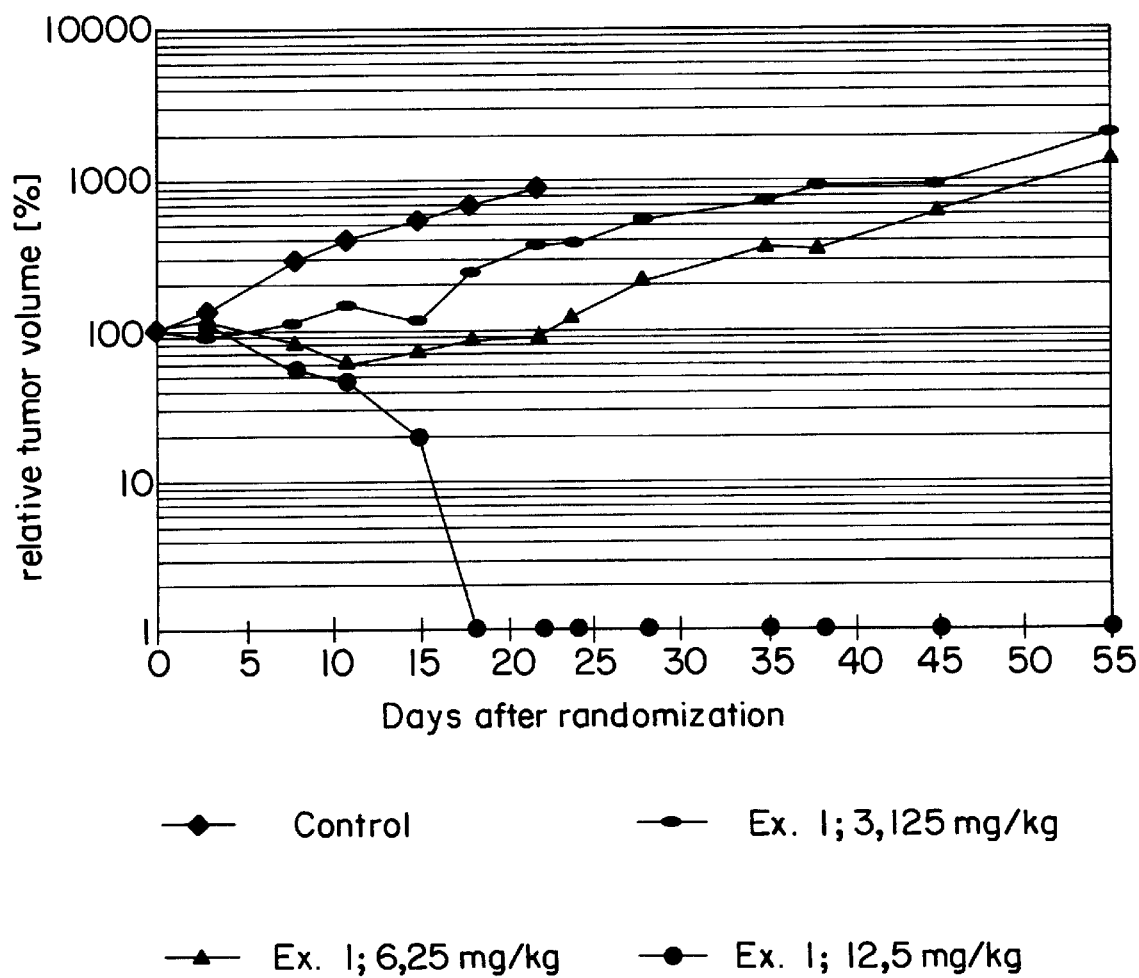

Narita et al., "Inhibition of beta–glucuronidase by natural glucuronides of Kampo medicines using glucuronide of SN–38 (7–ethyl–10–hydroxycamptothecin" as a substrate, Xenobiotica, vol. 23(1): 5–10, Jan. 1993.*

Takahashi et al., "The Role of Glucuronidation in 7–ethyl–10–hydroxycamptothecin Resistance in vitro", vol. 88: 1211–1217, Dec. 1997.*

Takasuna et al., "Protective Effects of Kampo Medicines and Baicalin against Intestinal Toxicity of a New Anticancer Camptothecin Derivative, Irinotecan Hydrochloride (CPT–11), in Rats", Jpn. J. Cancer Res., vol. 86: 978–984, Oct. 1995.*

Chu et al., "Multispecific Organ Anion Transporter is Responsible for the Biliary Excretion of the Camptothecin Derivative Irinotecan and its Metabolites in Rats", J. Pharm. Exp. Ther., vol. 281(1): 304–314, Jan. 1997.*

Jiang, J.; Li, W.–R.; Przeslawski, R. M.; and Joullie, M. M., "Comparative Study of Selected Reagents for Carboxyl Activation", Tetrahedron Letters,34(42): 6705–6708 (1993).

Wall, M. E.; Wani, M. C.; Cook C. E.; Palmer, K. H., "Plant Antitumor Agents. I. The Isolation and Structure of Camptothecin, a Novel Alkaloidal Leukemia and Tumor Inhibitor from *Camptotheca acuminata*", J. Am. Chem. Soc., 88(16): 3888–3890 (Aug. 1966).

* cited by examiner

20(S) CAMPTOTHECIN GLYCOCONJUGATES

This application is a 371 of PCT/EP98/02620, filed May 4, 1998.

The present invention relates to glycoconjugates of 20(S)-camptothecin, in which a 3-O-methylated β-L-fucose unit is linked to the 20-hydroxyl group of a camptothecin derivative via thiourea-modified peptide spacers. The invention furthermnore relates to processes for the preparation of the compounds according to the invention and to their use as medicaments, in particular in connection with oncoses.

20-(S)-Camptothecin is a pentacyclic alkaloid which was isolated in 1966 by Wall et al. (J. Am. Chem. Soc. 88, 3888 (1966)). It has a high antitumour active potential in numerous in vitro and in vivo tests. Unfortunately, however, the promising potential failed to be realized in the clinic because of toxicity and solubility problems.

By opening of the E ring lactone and formation of the sodium salt, a water-soluble compound was obtained which is in a pH-dependent equilibrium with the ring-closed form. Here too, clinical studies have been unsuccessful until now.

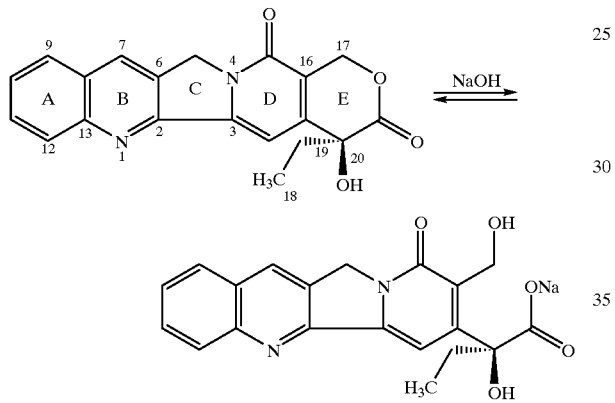

Approximately 20 years later, it was found that the biological activity is to be attributed to an enzyme inhibition of the topoisomerase I. Since then, the research activities have been increased again in order to find camptothecin derivatives which are more compatible and active in vivo.

To improve the water-solubility, salts of A ring- and B ring-modified camptothecin derivatives and of 20-O-acyl derivatives having ionizable groups have been described (Vishnuvajjala et al. U.S. Pat. No. 4,943,579). The latter prodrug concept was later also applied to modified camptothecin derivatives (Wani et al. WO 9602546). In vivo, however, the 20-O-acyl prodrugs described have a very short half-life and are very rapidly cleaved to give the parent structure.

WO 9631532 A1 describes sugar-modified cytostatics in which the linkage of various cytotoxic or cytostatically active compounds to, for example, regioselectively modified carbohydrate units via specific spacers lead to an improvement in the tumour selectivity. From the combinations of carbohydrate, spacer and active compound widely described there, we then surprisingly found that the linkage of β-L-fucose units modified in the 3-position via a thiourea-modified peptide spacer consisting of a sterically demanding non-polar side chain-containing and a basic side chain-containing amino acid on the 20-hydroxyl group of 20(S)-camptothecin leads to very particularly preferred conjugates having the following properties:

By means of the ester-like linkage of the carrier radical to the 20-hydroxyl group, the lactone ring in the camptothecin moiety, which is important for the action, is stabilized.

By means of the special conformation of the dipeptide spacers, the conjugates in extracellular medium and in blood have a stability which is again markedly improved in comparison with similar conjugates having other spacers previously described in WO 9631532. In particular, the conjugates according to the invention are more stable than the 20-O-acyl prodrugs of camptothecin described in U.S. Pat. No. 4,943,579.

The conjugates according to the invention have better water solubility in comparison with similar conjugates from WO 9631532.

In vitro, the conjugates according to the invention have a high activity against tumour cell lines and tumour xenografts.

In vivo, the conjugates according to the invention have excellent therapeutic activity over several dose stages against various tumours after i.v. administration.

Compared with the underlying toxophore they have a markedly higher tolerability and tumour selectivity, in particular with respect to bone marrow toxicity.

The invention relates to compounds of the formula (I)

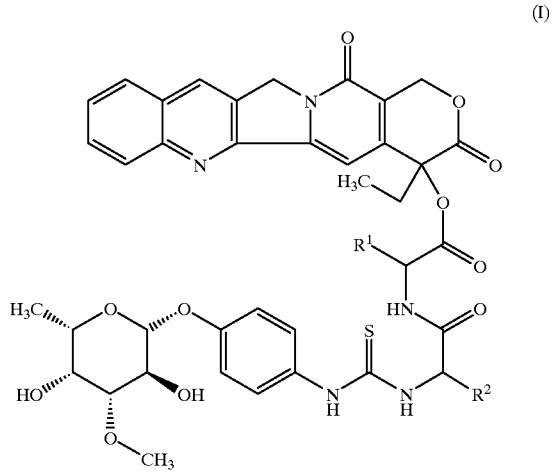

in which $R^1$ represents a sterically demanding non-polar side chain of an amino acid and $R^2$ represents a basic side chain of an amino acid and their salts, stereoisomers and stereoisomer mixtures.

Preferred compounds of the formula (I) are those in which $R^1$ is a branched alkyl radical having up to 4 carbon atoms and $R^2$ is a radical of the formula $-(CH_2)_n-R3$, where

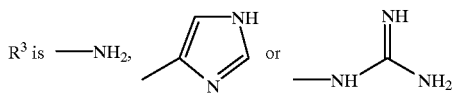

and n is a number 1 to 4.

Particularly preferred compounds of the general formula (I) are those in which

R¹ is a branched alkyl radical of the formula

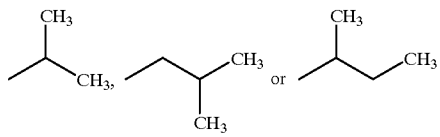

and

R² is a radical of the formula

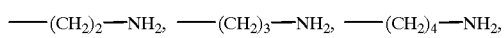

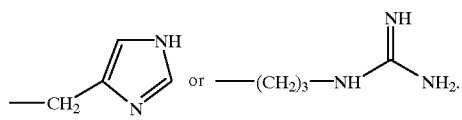

The camptothecin unit can be present in the 20(R) or in the 20(S) configuration or as a mixture of these two stereoisomeric forms. The 20(S) configuration is preferred.

The amino acids can occur in the L or in the D configuration or alternatively as a mixture of D and L form.

The term "amino acids" in particular designates the α-amino acids occurring in nature, but moreover also comprises their homologues, isomers and derivatives. As an example of isomers; enantiomers may be mentioned. Derivatives can be, for example, amino acids provided with protective groups.

Amino acids having "sterically demanding" side chains are understood as meaning those amino acids whose side chain has a branching in the β- or γ-position; examples which may be mentioned are valine and isoleucine or leucine.

Typical examples of amino acids having non-polar side chains which may be mentioned are:

alanine, valine, leucine, isoleucine, proline, tryptophan, phenylalanine, methionine.

Typical examples of amino acids having basic side chains which may be mentioned are:

lysine, arginine, histidine, ornithine, diaminobutyric acid.

The compounds according to the invention are preferably present in the form of their salts. In general, salts with organic or inorganic acids may be mentioned here.

The acids which can be adducted preferably include hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, trifluoroacetic acid, maleic acid, malonic acid, oxalic acid, gluconic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

The glycoconjugates according to the invention can be prepared, for example, by linkage of 20(S)-camptothecin to activated carboxyl components, which for their part can be moieties of protected amino acids, peptides or carbohydrate-modified peptides.

Preferably, the synthesis of the glycoconjugate takes place sequentially, beginning with the acylation of 20(S)-camptothecin with an N-protected carboxyl-activated unit of a non-polar sterically demanding amino acid in a suitable solvent, if appropriate in the presence of a base, according to customary methods. The amino protective group is then removed selectively by means of known methods. A unit of a basic amino acid, which, if necessary, is suitably protected is then linked and subsequently, if appropriate with retention of the side chain protective group, deblocked at the α-amino function. In the key step, the linkage to the carbohydrate radical is carried out by conversion of p-aminophenyl-3-O-methyl-β-L-fucopyranoside into the corresponding isothiocyanate and subsequent linkage to the deblocked α-amino group of the peptidyl camptothecin. Side chain protective groups which may still be present are detached and the free amino group is optionally converted into a suitable ammonium salt.

The invention thus furthermore relates to a process for the preparation of the glycoconjugates of the formula (I)

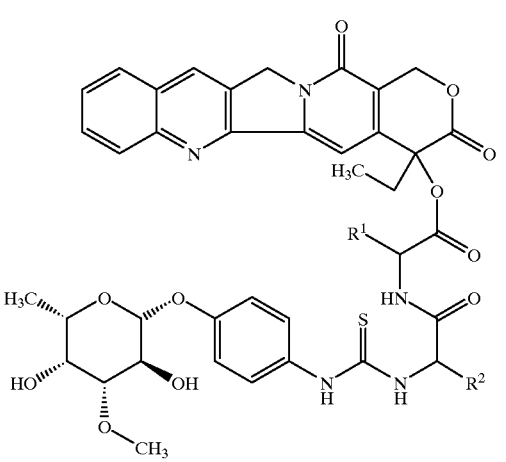

in which

R¹ represents a sterically demanding non-polar side chain of an amino acid and

R² represents a basic side chain of an amino acid, or of their salts, characterized in that the isothiocyanate of the formula (II)

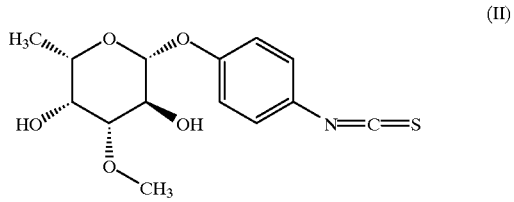

is reacted with the peptidyl-camptothecin, optionally bearing a protective group in the side chain, of the formula (III)

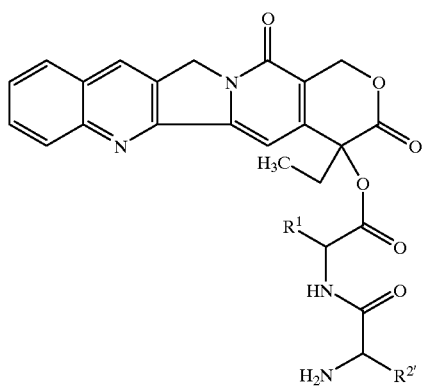

(III)

in which
R[1] has the abovementioned meaning and
R[2'] has the meaning of the abovementioned basic radical R[2], which moreover can carry a protective group customary in peptide chemistry on the basic group
to give the glycoconjugate of the formula (IV)

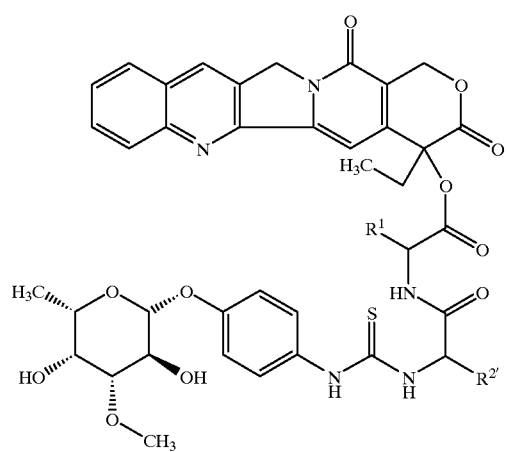

(IV)

in which
R[1] and R[2'] have the meanings indicated above,
the side chain amino protective group which may be present is removed according to customary methods and the compound obtained is optionally converted into the desired salt.

Another sequence of reaction steps in the synthesis of the target compound is also conceivable. Thus, according to a likewise preferred variant, the p-isothiocyanatophenyl-3-O-methyl-β-L-fucoside can also be linked first with the optionally suitably protected terminal basic amino acid, and this unit can then be reacted with the free amino group of the amino acid conjugate of 20(S)-camptothecin and the nonpolar, sterically demanding amino acid. Side chain protective groups which may be present are detached and the free amino group is optionally converted into a suitable ammonium salt.

The invention therefore further relates to an alternative process for the preparation of compounds of the general formula (I) or of their salts, characterized in that the isothiocyanate of the formula (II)

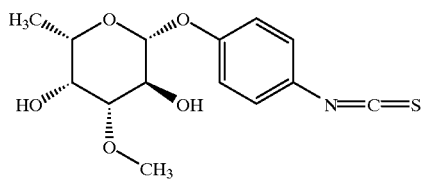

(II)

is reacted with an optionally suitably protected terminal basic amino acid of the formula (V)

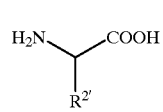

(V)

in which R[2'] represents a basic side chain of an amino acid whose basic group can be protected,
to give an amino acid conjugate of the formula (VI)

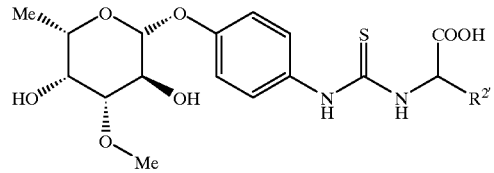

(VI)

in which R[2'] has the meaning indicated above,
this is then reacted with amino acid conjugates of the formula (VII)

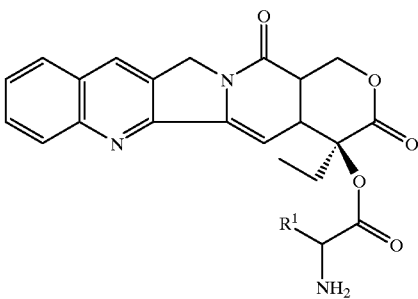

(VII)

in which R[1] has the meaning indicated above,
the side chain protective group is removed and the compounds are optionally converted into a suitable salt.

Diastereomer mixtures can be formed, in particular after linkage of the first amino acid to camptothecin. Pure diastereomers of the compounds according to the invention can be prepared by the process indicated above, for example, by separating the diastereomers in a suitable manner after linkage of the first amino acid unit to the camptothecin and subsequent protective group removal. The diastereomerically pure target compound can be prepared from a diastereomerically pure intermediate compound by the route indicated above.

The diastereomer mixture of the target compound can also be separated into the individual diastereomers in a customary manner.

The reactions can be carried out under various pressure and temperature conditions, for example 0.5 to 2 bar, and −30 to +100° C., in suitable solvents such as dimethylformamide (DMF), tetrahydrofuran (THF), dichloromethane, chloroform, lower alcohols, acetonitrile, dioxane, water or in mixtures of the solvents mentioned. As a rule, reactions in DMF, dichloromethane or THF/dichloromethane at room temperature and normal pressure are preferred.

For the activation of the carboxyl groups, possible coupling reagents are those known in peptide chemistry such as described, for example, in Jakubke/Jeschkeit: Aminosäuren, Peptide, Proteine (Amino Acids, Peptides, Proteins); Verlag Chemie 1982 or Tetrahedr. Lett. 34, 6705 (1993). N-Carboxylic anhydrides, acid chlorides or mixed anhydrides, for example, are preferred.

Furthermore suitable for the activation of the carboxyl groups is the formation of adducts with carbodiumides, e.g. N,N'-diethyl-, N,N'-diisopropyl-, N,N'-dicyclohexylcarbodiimide, N-(3-dimethylaminopropyl)-N'-ethyl-carbodiumide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris-(dimethylamino)-phosphonium hexafluorophosphate, 1-hydroxybenzotriazole esters or N-hydroxysuccinimide esters. Furthermore, the amino acid components can also be employed in the form of a Leuch' anhydride.

Bases employed can be, for example, triethylamine, ethyldiisopropylamine, pyridine, N,N-dimethylaminopyridine or others.

Protective groups employed for third functions of the amino acids can be the protective groups known in peptide chemistry, for example of the urethane, alkyl, acyl, ester or amide type.

Amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyt, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl (Boc), allyloxycarbonyl, vinyloxycarbonyl, 3,4,5-trimethoxybenzyloxycarbonyl, phthaloyl, 2,2,2-trichloroethoxycarbonyl, 2,2,2-trichloro-tert-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. The Fmoc group and the Boc group are particularly preferred.

Preferred carboxyl protective groups are linear or branched $C_1$- to $C_4$-alkyl esters.

The removal of protective groups in appropriate reaction steps can be carried out, for example, by reaction of acid or base, hydrogenolytically or reductively in another manner.

Both in vitro and in vivo, the glycoconjugates according to the invention have a surprisingly strong antitumour activity against various tumours, in particular lung, breast, pancreas, melanoma and large intestine tumours, combined with a great selectivity against non-malignant cells.

They are therefore suitable for the treatment of oncoses, to be specific both in human and in veterinary medicine.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compounds can optionally be present in one or more of the excipients indicated above and also in microencapsulated form.

The therapeutically active compounds should be present in the abovementioned pharmaceutical preparations in a concentration from approximately 0.1 to 99.5, preferably from approximately 0.5 to 95%, by weight of the total mixture.

Apart from the compound according to the invention, the abovementioned pharmaceutical preparations can also contain further pharmaceutical active compounds.

In general, it has proven advantageous both in human and in veterinary medicine to administer the active compound according to the invention in total amounts of approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts from approximately 1 to 80, in particular 3 to 30, mg/kg of body weight.

BIOLOGICAL TESTING

1. Growth Inhibition Test for the Determination of the Cytotoxic Properties:

The human large intestine cell lines SW 480 and HT 29 (ATCC No. CCL 228 and HBT 38) and the mouse melanoma cell line B16F10 (CRL 6475) were grown in Roux dishes in RPMI 1640 medium with addition of 10% FCS. They were then trypsinized and taken up in RPMI plus 10% FCS to a cell count of 50,000 cells/ml for SW 480 and HT 29 and 20,000 cells for B16F10. 100 µl of cell suspension/well were added to a 96 microwell plate and incubated for 1 day at 37° C. in a $CO_2$ incubator. A further 100 µl of RPMI medium and 1 µl of DMSO containing the test substances were then added. The growth was checked after day 6. To do this, 25 µl of MTT solution (3-(4,5-dimethylthiazol-2-yl)-2,5-diphenyltetrazolium bromide) having a starting concentration of 5 mg/ml of $H_2O$ were added to each microwell. Incubation was carried out for 5 hours in a $CO_2$ incubator at 37° C. The medium was then aspirated and 100 µl of i-propanol/well were added. After shaking for 30 min with 100 µl of $H_2O$, the extinction was measured at 595 nm using a multiplate reader (Bio.) 3550 UV.

The cytotoxic action is indicated in Table 1 as the $IC_{50}$ value in each case for the SW 480 and HT 29 and B16F10 cell lines:

TABLE 1

| Example | $IC_{50}$/nM SW 480 | $IC_{50}$/nM HT 29 | $IC_{50}$/nM B16F10 |
|---|---|---|---|
| 20(S)-Camptothecin | 10 | 5 | 20 |
| Example 1 | 70 | 40 | 200 |
| Example 2 | 100 | 40 | 300 |
| Example 3 | 100 | 20 | 500 |

TABLE 1-continued

| Example | IC$_{50}$/nM SW 480 | IC$_{50}$/nM HT 29 | IC$_{50}$/nM B16F10 |
|---|---|---|---|
| Example 4 | 100 | 20 | 500 |
| Example 5 | 80 | 50 | 200 |
| Example 6 | 60 | 30 | 300 |
| Example 7 | 80 | 30 | 20 |
| Example 8 | 200 | 100 | 800 |
| Example 9 | 200 | 70 | 400 |
| Example 10 | 100 | 50 | 300 |

2. Haematopoetic Activity of the Glycoconjugate in Comparison with the Underlying Active Compound:

Material and Methods:

Bone marrow cells were washed out of mice femurs. $10^5$ cells were incubated at 37° C. and 7% $CO_2$ in McCoy 5A medium (0.3% agar) together with recombinant murine GM-CSF (Genzyme; stem cell colony formation) and the substances ($10^{-4}$ to 100 μg/ml). 7 days later, the colonies (<50 cells) and clusters (17–50 cells) were counted.

Results:

As shown in Tab. 2, the glycoconjugates investigated show a drastically reduced inhibition of the bone marrow stem cell proliferation compared with the underlying active compound.

TABLE 2

Inhibition of the CSF-induced proliferation of mouse bone marrow stem cells

| | IC$_{50}$ [ng/mL] |
|---|---|
| 20(S)-Camptothecin | 0.05 |
| Example 1 | 15 |
| Example 2 | 30 |
| Example 3 | 15 |
| Example 4 | 15 |
| Example 5 | 20 |
| Example 6 | 10 |
| Example 7 | 8 |
| Example 8 | 45 |
| Example 9 | 15 |
| Example 10 | 30 |

3. In Vivo Inhibition of Tumour Growth in the Nude Mouse Model

Material:

For all in vivo experiments for investigation of the inhibition of tumour growth, athymic nude mice (NMRI nu/nu strain) were used. The selected large-cell lung carcinoma LXFL 529 was grown by serial passage in nude mice. The human origin of the tumour was confirmed by isoenzymatic and immunohistochemical methods.

Experimental Set-up:

The tumour was implanted subcutaneously into both flanks of small nu/nu nude mice 6 to 8 weeks old. The treatment was started, depending on the doubling time, as soon as the tumours had reached a diameter of 5–7 mm. The mice were assigned to the treatment group and the control group (5 mice per group with 8–10 assessable tumours) by randomization. The individual tumours of the control group all grew progressively.

The size of the tumours was measured in two dimensions by means of a slide gauge. The tumour volume, which correlated well with the cell count, was then used for all evaluations. The volume was calculated according to the formula "length×breadth×breadth/2" ([a×b$^2$]/2, a and b represent two diameters at right angles).

The values of the relative tumour volume (RTV) were calculated for each individual tumour by dividing the tumour size on day X with the tumour size on day 0 (at the time of randomization). The mean values of the RTV were then used for the further evaluation.

The inhibition of the tumour volume (relative tumour volume of the test group/control group×100, T/C in %) was the final measured value.

Treatment:

The administration of the compounds was carried out intravenously (i.v.), for example on day 0, 1 and 2 after randomization, the total dose per day being split over 2 administrations.

Results:

The therapeutic efficacy of the glycoconjugates according to the invention from Examples 1 and 2 is shown by way of example in the large-cell human lung tumour xenograft LXFL 529. In the case of the maximum tolerable dose (MTD) and at ½ MTD, the therapy leads to complete to marked tumour remission. An excellent action can also be demonstrated on other tumours.

TABLE 3

| Therapy | Dose [mg/kg/day] | Survival time [days] | T/C [%] | Number of tumours | opt. T/C [%] | Relative body weight on day 7 [% of day 0] |
|---|---|---|---|---|---|---|
| Control | — | 7<br>>28<br>>28 | >28<br>>28 | 8 | 100 | 104 |
| Example 1 | 16 | >28<br>>28<br>>28 | >28<br>>28 | 10 | 0<br>(day 28) | 95 |
| Example 1 | 8 | 0<br>>28<br>>28 | >28<br>>28 | 8 | 0<br>(day 14) | 95 |
| Example 2 | 32 | >28<br>>28<br>1 | >28<br>20 | 8 | 0<br>(day 21) | 98 |
| Example 2 | 16 | >28<br>>28<br>>28 | >28<br>>28 | 8 | 3.3<br>(day 28) | 103 |

The long-lasting complete remission of the compound from Example 1 in the dose range from 16 to 8 mg/kg and the dose-dependence of the action is shown in a further experiment in FIG. 1 using the therapy schedule day 1–3 i.v.

4. Hydrolytic Stability:

The compounds according to the invention from Examples 1, 2, 8 and 9 are dissolved in water and, after standing at room temperature for 24 h, show markedly less than 1% camptothecin release in the HPLC according to area percent.

On dissolving 10 μM of the compounds from Examples 1 and 2 in RPMI medium plus 10% FCS and in 30% strength human whole blood in PBS buffer, only a camptothecin release of less than 5% took place after standing for 24 h.

Method:

HPLC system Hewlett Packard HP 1050

Column: Nucleosil 120-5 C 18 250 mm×4 mm (Macherey & Nagel; Germany)

Eluent: A: 0.01 M $KH_2PO_4$ in $H_2O$ ($H_2$=Milli-pore grade)
B: 80% acetonitrile/20% eluent A Flow rate: 1.2 ml Gradient: $t_0$: 20% B–$t_{40}$: 100% B
$t_{45}$: 100% B–$t_{47}$: 20% B Detection: 240 nm or 370 nm 5. Lactone Stabilization:

The glycoconjugates according to the invention from Examples 1, 2 8 and 9 are dissolved in 80% water and 20% of acetonitrile and adjusted to pH 9 using 2 equivalents of sodium hydroxide solution. After standing at room temperature for 1 h, the lactone ring opening is less than 5% (detection according to the above method).

EXAMPLES

Carbohydrate Starting Material

I) p-Aminophenyl-3-O-methyl-β-L-fucopyranoside:

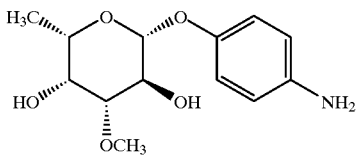

I.a) p-Nitrophenyl-3-O-methyl-β-L-fucopyranoside:

6 g (21 mmol) of p-nitrophenyl-β-L-fucopyranoside in 300 ml of absol. methanol are treated with 7.84 g (31.5 mmol) of dibutyltin oxide and heated under reflux for 2 h. The mixture is then concentrated, and the residue is dried and then taken up in 300 ml of DMF. After addition of 15.7 ml of methyl iodide, the batch is stirred at 70° C. for 40 h. The solvent is removed in vacuo and the residue is taken up in 300 ml of dichloromethane. The suspension is filtered, and the remaining solution is concentrated again and subjected to flash chromatography (dichloromethane/methanol 99:1). After concentration, 3.82 g (61%) of the target product are obtained.

I.) p-Aminophenyl-3-O-methyl-β-L-fucopyranoside:

3.81 g (12.73 mmol) of p-nitrophenyl-3-O-methyl-β-L-fucopyranoside are dissolved in methanol and, after addition of platinum dioxide, hydrogenated in a hydrogen atmosphere at a slight overpressure. After filtering off the catalyst and precipitating with ether, 3 g (88%) of the target product are obtained. [TLC: dichloromethane/methanol 9:1 $R_f$=0.53].

Peptidyl-camptothecin Starting Materials

II) 20(S)-20-O-{N$^\epsilon$-[Fluorenyl-9-methoxycarbonyl]-L-lysyl-L/D-leucyl}-camptothecin, trifluoroacetate:

II) L 20(S)-20-O-{N$^\epsilon$-[Fluorenyl-9-methoxycarbonyl]-L-lysyl-L-leucyl}-camptothecin, trifluoroacetate:

II) D 20(S)-20-O-{N$^\epsilon$-[Fluorenyl-9-methoxycarbonyl]-L-lysyl-D-leucyl}-camptothecin, trifluoroacetate:

I.a) 20(S)-20-O-[N-(tert-Butoxycarbonyl)-L/D-leucyl]-camptothecin:

A suspension of 10 g (28.7 mmol) of 20(S)-camptothecin in 250 ml of absolute dimethylformamide is treated with stirring with 11.1 g (43 mmol) of N-(tert-butoxycarbonyl)-leucine-N-carboxylic anhydride and 1 g of 4-(N,N-dimelthylamino)-pyridine. After treatment for 16 h in an ultrasonic bath at room temperature, a further 3.7 g of N-(tert-butoxycarbonyl)-leucine-N-carboxylic anhydride are added and the mixture is left at room temperature for a further 2 h. It is then separated off from the residual undissolved camptothecin and the filtrate is concentrated in vacuo. The residue is purified by flash chromatography [petroleum ether/ethyl acetate 1:1->1:4]. 13.55 g (84%) of the target compound IIa) are obtained. [TLC: acetonitrile $R_f$=0.47].

II.b) 20(S)-20-O-L/D-Leucyl-camptothecin, trifluoroacetate:

II.b) L 20(S)-20-O-L-Leucyl-camptothecin, trifluoroacetate:

II.b) D 20(S)-20-O-D-Leucyl-camptothecin, trifluoroacetate:

A solution of compound II.a (13.55 g, 24.1 mmol) in a mixture of 100 ml of dichloromethane and 40 ml of anhydrous trifluoroacetic acid is stirred at room temperature for 30 min. After concentrating in vacuo to a small volume, the product is precipitated with diethyl ether and thoroughly washed with diethyl ether. A double spot with $R_f$ values of 0.4 and 0.32 is detected in the thin-layer chromatogram (acetonitrile/water 20:1) [Yld.: 9.5 g (68%)].

By precipitating several times from dichloromethane/methanol using diethyl ether, the mixture can be separated into two individual components II.b) L and II.b) D. Both forms prove to be diastereomers which produce slightly different $^1$H-NMR spectra:

| Polar diastereomer: | |
|---|---|
| 400-MHz-$^1$H—NMR (CD$_2$Cl$_2$/CD$_3$OD 1:1):δ | s C—H (B-ring) 8.63 ppm |
| | s C—H (D ring) 7.4 ppm |
| Non-polar diastereomer: | |
| 400-MHz-$^1$H—NMR (CD$_2$Cl$_2$/CD$_3$OD 1:1):δ | s C—H (B-ring) 8.60 ppm |
| | s C—H (D ring) 7.32 ppm |

In the further stages, either the mixture of the two forms or the purified diastereomerically pure forms can be employed.

II.c) 20(S)-20-O-[N$^\alpha$-(tert-Butoxycarbonyl)-N$^\epsilon$-(fluorenyl-9-methoxy-carbonyl)-L-lysyl-L/D-leucyl]-camptothecin:

II.c) L 20(S)-20-O-[N$^\alpha$-(tert-Butoxycarbonyl)-N$^\epsilon$-(fluorenyl-9-methoxycarbonyl)-L-lysyl-L-leucyl]-camptothecin:

II.c) D 20(S)-20-O-[N$^\alpha$-(tert-Butoxycarbonyl)-N$^\epsilon$-(fluorenyl-9-methoxycarbonyl)-L-lysyl-D-leucyl]-camptothecin:

25.6 g (54.6 mmol) of [N$^\alpha$-(tert-butoxycarbonyl)-N$^\epsilon$-(fluorenyl-9-methoxycarbonyl)-L-lysine and 11.1 g (82 mmol) of 1-hydroxy-1H-benzotriazole hydrate are dissolved in 500 ml of dimethylformnamide. After addition of 12.6 g (1.2 eq.) of N-ethyl-N'-(dimethylaminopropyl)-carbodiimide hydrochloride, the mixture is stirred at room temperature for 1 h. Compound II.b (26.2 g, 0.83 eq.) and 7.83 ml (1 eq.) of ethyl-diusopropylamine are then added and the batch is stirred at room temperature for a further 16 h. After concentration in vacuo and purification by flash chromatography [petroleum ether/ethyl acetate 1:2->ethyl acetate], the target compound (43.5 g, 87%) is obtained [TLC: acetonitrile $R_f$=0.44].

As in the farther examples too, the batch can also be carried out completely analogously with each of the purified diastereomenrcally pure forms in II.b.

II) 20(S)-20-O-{N$^\epsilon$-[Fluorenyl-9-methoxycarbonyl]-L-lysyl-L/D-leucyl}-camptothecin, trifluoroacetate:

II) L 20(S)-20-O- {N$^\epsilon$-[Fluorenyl-9-methoxycarbonyl]-L-lysyl-L-leucyl}-camptothecin, trifluoroacetate II) D 20(S)-20-O-{N$^\epsilon$-[Fluorenyl-9-methoxycarbonyl]-L-lysyl-D-leucyl}-camptothecin, trifluoroacetate The compound II.c (43.3 g, 47.5 mmol) is taken up in 150 ml of dichloromethane and treated with 50 ml of anhydrous trifluoroacetic acid. The resulting solution is stirred at room temperature for 1 h. After concentrating to a small volume in vacuo, the product is precipitated by addition of diethyl ether. 39.4 g (90%) of the target compound are obtained [TLC: acetonitrile/water 10:1 R$_f$=0.35].

III) 20(S)-20-O-(L-Histidyl-L/D-valyl)-camptothecin, trifluoroacetate:

III.a) 20(S)-20-O-[N-tert-Butoxycarbonyl)-L/D-valyl)-camptothecin:

A suspension of 10 g (28.7 mmol) of 20(S)-camptothecin in 500 ml of absolute dimethylformamide is treated with stirring with 21.5 g (3 equivalents) of N-(tert-butoxycarbonyl)-vatine-N-carboxylic anhydride and 1 g of 4-(N,N-dimethylamino)-pyridine. After treatment for 16 h in an ultrasonic bath at room temperature, residual undissolved camptothecin is separated off and the filtrate is concentrated in vacuo. The residue is purified by flash chromatography [petroleum ether/ethyl acetate 1:3->ethyl acetate]. 11.65 g (73%) of the target compound are obtained. {TLC: acetonitrile R$_f$=0.44]. If the same reaction is carried out under reflux conditions in dichloromethane instead of in dimethylformamide, the formation of the diastereomer with the L configuration of the valine unit is strongly favoured.

III.b) 20(S)-20-O-L/D-Valyl-camptothecin, trifluoroacetate:

III.b) L 20(S)-20-O-L-Valyl-camptothecin, trifluoroacetate

III.b) D 20(S)-20-O-D-Valyl-camptothecin, trifluoroacetate

A solution of compound III.a (11.65 g, 21 mmol) in a mixture of 100 ml of dichloromethane and 100 ml of anhydrous trifluoroacetic acid is stirred at room temperature for 1 h. After concentrating in vacuo to a small volume, the product is precipitated with diethyl ether and washed thoroughly with diethyl ether. The product is again precipitated from dichloromethane/methanol with diethyl ether and isolated as a mixture of diastereomeric forms. Yld.: 10.9 g (92%) [TLC: acetonitrile/water 20:1 R$_f$=0.31 and 0.39]. A greater purification of the non-polar diastereomer having the L-configuration of the valine unit is possible in this stage by crystallization from methanol:

8 g of the resulting product having the enriched non-polar diastereomer are dissolved in 80 ml of methanol, cooled to 0° C. and treated with diethyl ether in 10 ml steps. After addition of a total of 60 ml of diethyl ether, the precipitated product is filtered off with suction and dried. 4.6 g (58%) of pure non-polar diastereomer having the L-configuration of the valine unit are obtained. A reprecipitation of the mother liquor with diethyl ether affords a further 730 mg (9%) of a product fraction having a diastereomer ratio of 1:18.

In the further reactions, both the diastereomer mixture and the purified non-polar or the polar diastereomer can be employed. The reactions proceed completely analogously.

III.c) 20(S)-20-O-[N-tert-Butoxycarbonyl)-L-histidyl-L/D-valyl]-camptothecin:

III.c) L 20(S)-20-O-[N-tert-Butoxycarbonyl)-L-histidyl-L-valyl]-camptothecin

III.c) D 20(S)-20-O-[N-tert-Butoxycarbonyl)-L-histidyl-D-valyl]-camptothecin 5.95 g (23.3 mmol) of N-(tert-butoxycarbonyl)-L-histidine and 4.73 g of 1-hydroxy-1H-benzotriazole hydrate are dissolved in 200 ml of dimethylformamide. After addition of 5.38 g of N-ethyl-N'-(dimethylaminopropyl)-carbodiimide hydrochloride, the mixture is stirred at room temperature for 1 h. Compound III.b (10.9 g, 19.44 mmol) and 6.7 ml of ethyl-diisopropylamine are then added and the batch is stirred at room temperature for a further 16 h. After concentration in vacuo and purification by flash chromatography [acetonitrile/water 50:1->20:1], the target compound is obtained [TLC: acetonitrile/water 10:1 R$_f$=0.42], which is immediately reacted further.

III) 20(S)-20-O-(L-Histidyl-L/D-valyl)-camptothecin, bis-trifluoroacetate:

III) L 20(S)-20-O-(L-Histidyl-L-valyl)-camptothecin, bis-trifluoroacelate

III) D 20(S)-20-O-(L-Histidyl-D-valyl)-camptothecin, bis-trifluoroacetate

The compound III.c is taken up in 100 ml of dichloromethane and treated with 50 ml of anhydrous trifluoroacetic acid. The resulting solution is stirred at room temperature for 30 min. After concentrating to a small volume in vacuo, the product is precipitated by addition of diethyl ether. 13.05 g (83%) of the target compound are obtained [TLC: acetonitrile/water/glacial acetic acid 5:1:0.2 R$_f$=0.2].

IV) 20(S)-20-O-{N$^\epsilon$-[Fluorenyl-9-methoxycarbonyl]-D-tysyl-L/D-leucyl}-camptothecin, trifluoroacetate:

IV) L 20(S)-20-O-{N$^\epsilon$-[Fluorenyl-9-methoxycarbonyl]-D-lysyl-L-leucyl}-camptothecin, trifluoroacetate:

IV) D 20(S)-20-O-{N$^\epsilon$-[Fluorenyl-9-methoxycarbonyl]-D-lysyl-D-leucyl}-camptothecin, trifluoroacetate:

The synthesis of this compound is carried out in complete analogy to the diastereomeric compound II. In stage II.c, instead of N$^\alpha$-(tert-butoxycarbonyl)-N$^\epsilon$-(fluorenyl-9-methoxycarbonyl)-L-lysine the corresponding D isomer is employed [TLC: acetonitrile/water 10:1 R$_f$=0.4].

V) 20(S)-20-O-{N$^\epsilon$-[Fluorenyl-9-methoxycarbonyl]-L-ornithyl-L/D-leucyl}-camptothecin, trifluoroacetate:

V) L 20(S)-20-O-{N$^\epsilon$-[Fluorenyl-9-methoxycarbonyl]-L-ornithyl-L-leucyl}-camptothecin, trifluoroacetate V) D 20(S)-20-O-{N$^\epsilon$-[Fluorenyl-9-methoxycarbonyl]-L-ornithyl-D-leucyl}-camptothecin, trifluoroacetate The synthesis of this compound is carried out in complete analogy to the corresponding lysine compound II. In stage II.c, instead of N$^\alpha$-(tert-butoxycarbonyl)-N$^\epsilon$-(fluorenyl-9-methoxycarbonyl)-L-lysine N$^\alpha$-(tert-butoxycarbonyl)-N$^\epsilon$-(fluorenyl-9-methoxycarbonyl)-L-ornithine is employed. [TLC: acetonitrile/water 20:1 R$_f$=0.125].

VI) 20(S)-20-O-(L-Arginyl-L/D-leucyl}-camptothecin, tri-trifluoroacetate:

VI) L 20(S)-20-O-{L-Arginyl-L-leucyl}-camptothecin, tri-trifluoroacetate

VI) D 20(S)-20-O-{L-Arginyl-D-leucyl}-camptothecin, tri-trifluoroacetate

VI.a) 20(S)-20-O-(Tri-tert-butoxycarbonyl-L-arginyl-L/D-leucyl)-camptothecin:

VI.a) L 20(S)-20-O-{Tri-tert-butoxycarbonyl-L-arginyl-L-leucyl}-camptothecin

VI.a) D 20(S)-20-O-{Tri-tert-butoxycarbonyl-L-arginyl-D-leucyl}-camptothecin 200 mg (0.42 mmol) of tri-tert-butoxycarbonyl-L-arginine and 80 mg of 1-hydroxy-1H-benzotriazole hydrate are dissolved in 20 ml of dimethylformamide. After addition of 97 mg of N-ethyl-N'-(dimethylaminopropyl)-carbodiimide hydrochloride, the mixture is stirred at room temperature for 1 h. Compound II.b (200 mg, 0.35 mmol) and 217 μl of ethyl-diisopropylamine are then added and the batch is stirred at room temperature for a further 3 d. After concentrating in vacuo and treating with water, the target compound is obtained [TLC: acetonitrile/water 5:1:0.2 $R_f$=0.77], which is immediately reacted further.

VI) 20(S)-20-O-{L-Arginyl-L/D-leucyl}-camptothecin, tri-trifluoroacetate:

VI) L 20(S)-20-O-{L-Arginyl-L-leucyl}-camptothecin, tri-trifluoroacetate

VI) D 20(S)-20-O-{L-Arginyl-D-leucyl}-camptothecin, tri-trifluoroacetate 0.35 mmol of the compound from VI.a) is stirred at room temperature for 2 h with 5 ml of anhydrous trifluoroacetic acid in 10 ml of dichloromethane. The mixture is concentrated and reprecipitated twice from dichloromethane/methanol using diethyl ether. 280 mg (82%) of the target compound are obtained [TLC: acetonitrile/water 10:3:1.5 $R_f$=0.42].

VII) L 20(S)-20-O-{N$^\epsilon$[-Fluorenyl-9-methoxycarbonyl]-L-lysyl-L-valyl}-camptothecin, trifluoroacetate:

VII.a) L 20(S)-20-O-[N$^\alpha$-(tert-butoxycarbonyl)-N$^\epsilon$-(fluorenyl-9-methoxycarbonyl)-L-lysyl-L-valyl}-camptothecin:

10.02 g (21 .4 mmol) of N-(tert-butoxycarbonyl)-N-(fluorenyl-9-methoxycarbonyl)-L-lysine and 4.4 g (32.1 mmol) of 1-hydroxy-1H-benzotriazole hydrate are dissolved in 400 ml of dimethylformamide. After addition of 4.92 g (1.2 eq.) of N-ethyl-N'-(dimethylaminopropyl)-carbodiimide hydrochloride, the mixture is stirred at 0° C. for 30 min. 10 g (17.8 mmol) of the non-polar diastereomer III.b L of compound III.b and 9.2 ml (3 eq.) of ethyl-diisopropylamine are then added and the mixture is stirred at room temperature for a further 16 h. After concentrating in vacuo, the residue is stirred with 500 ml of water for 30 min and filtered off with suction. The product is taken up in 400 ml of dichloromethane, the residual water is removed, and the solution is concentrated to 200 ml and then precipitated with 800 ml of diethyl ether. The residue is filtered off with suction and washed with diethyl ether. 14.712 g of the target compound are obtained (92%) [TLC: acetonitrile $R_f$=0.6].

VII) L 20(S)-20-O-{N-[Fluorenyl-9-methoxycarbonyl]-L-lysyl-L-valyl}-camptothecin, trifluoroacetate:

The compound VII.a) L (14.65 g, 16.3 mnol) is taken up in 300 ml of dichloromethane and treated with 50 ml of anhydrous trifluoroacetic acid at 0° C. The resulting solution is stirred with ice-cooling for 2 h. After concentrating to a small volume in vacuo, the product is precipitated by addition of diethyl ether. 13.8 g (93%) of the target compound are obtained [TLC: acetonitrile/water 10:1. $R_f$=0.35].

Example 1

20(S)-20-O-{N$^\alpha$-[O-(3-O-Methyl-β-L-fucopyranosyl)-4-hydroxy-phenylamino-thiocarbonyl]-L-lysyl-L/D-leucyl}-camptothecin, hydrochloride

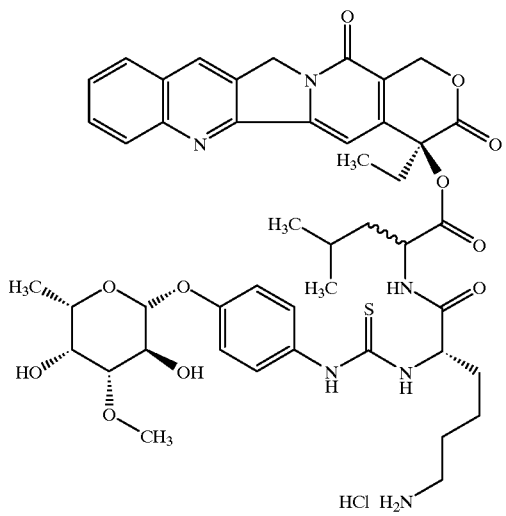

1.a) 20(S)-20-O-{N$^\alpha$-[O-(3-O-Methyl-β-L-fucopyranosyl)-4-hydroxy-phenylamino-thiocarbonyl]-N$^\epsilon$-[fluorenyl-9-methoxycarbonyl)-L-lysyl-L/D-leucyl}-camptothecin:

A solution of 9.82 g (36.5 mmol) of p-aminophenyl-3-O-methyl-β-L-fucopyranoside (Example I) in 500 ml of dioxane/water 1:1 is treated with stirring with 3.94 ml of thiophosgene (1.4 eq.). After 10 min, the mixture is treated with 4 equivalents of ethyldiisopropylamine, then concentrated in vacuo and the residue is dried for 1 h in an oil pump vacuum. The isothiocyanate obtained is dissolved in 500 ml of absolute dimethylformamide and treated with 30.4 g (32.8 mmol) of compound II and 22.6 ml of ethyldulsopropylamine. The mixture is stirred at room temperature for 16 h, then concentrated in vacuo and stirred with water. The residue is purified by flash chromatography [acetonitrile->acetonitrile/water 30:1]. The product is reprecipitated from dichloromethane/methanol using diethyl ether and washed with diethyl ether. 28.7 g (78%) of the target product are obtained [TLC: acetonitrile/water 10:1 $R_f$=0.44].

1.b) 20-O-{N$^\alpha$-[-O-(3-O-Methyl-β-L-fucopyranosyl)-4-hydroxy-phenylamino-thiocarbony]-L-lysyl-L/D-leucyl}-camptothecin:

28.6 g (25.5 mmol) of the conjugate 1.a) are treated with 5 ml of piperidine in 200 ml of dimethylfonmamide. After stirring at room temperature for 2 h, the mixture is concentrated and the residue is digested twice with dichloromethane and diethyl ether is added. It is then taken up in dimethylformnamide/dichloromethane and precipitated with ether. This purification process is repeated twice. The product is filtered off with suction and washed with ether. Yld.: 19.5 g (85%) [TLC: acetonitrile/water/glacial acetic acid 5:1:0.2 $R_f$=0.3].

1) 20(S)-20-O-{N$^\alpha$-[O-(3-O-Methyl-β-L-fucopyranosyl)-4-hydroxy-phenylamino-thiocarbonyl]-L-lysyl-L/D-leucyl}-camptothecin, hydrochloride:

10 g (11.1 mmol) of the compound from Example 1.b are taken up in 100 ml of water, treated with 11.1 ml (1 eq.) of a 1N HCl solution and lyophilized. The product is then precipitated several times from dichloromethane/methanol using diethyl ether. Yld.: 9.15 g (88%) [TLC: acetonitrile/water/glacial acetic acid 5:1:0.2 R$_f$=0.3].

Example 2

20(S)-20-O-{N-[O-(3-O-Methyl-β-L-fucopyranosyl)-4-hydroxy-phenylamino-thiocarbonyl]-L-histidyl-L/D-valyl}-camptothecin, hydrochloride

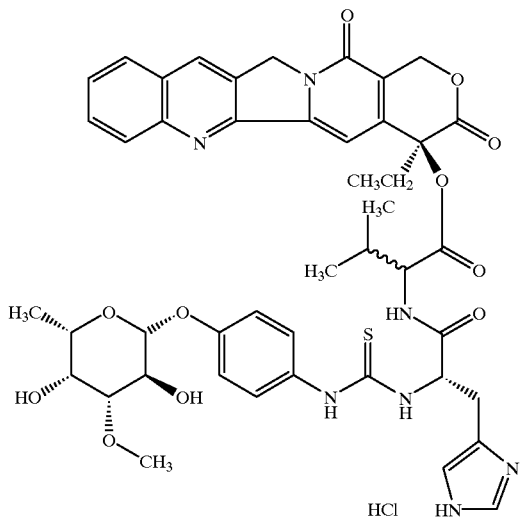

A solution of 7.14 g (26.5 mmol) of p-aminophenyl-3-O-methyl-β-L-fucopyranoside (carbohydrate starting material I) in 300 ml of dioxane/water 1:1 is treated with stirring with 2.86 ml of thiophosgene (1.4 eq.). After 10 min, the mixture is treated with 4 equivalents of ethyldiisopropylamine, then concentrated in vacuo and the residue is dried for 1 h in an oil pump vacuum. The isothiocyanate obtained is dissolved in 500 ml of absolute dimethylformamide and treated with 17.45 g (22 mmol) of compound III and 22.7 ml of ethyldiisopropylamine. The mixture is stirred at room temperature for 16 h, then concentrated in vacuo and the residue is taken up in water. It is adjusted to pH 7.8 using 1N aqueous sodium hydroxide solution and the solid is filtered off with suction. After drying in a high vacuum, the residue is reprecipitated twice from dichloromethane/methanol using diethyl ether and washed with diethyl ether. 17.97 g (91%) of the target product are obtained, which is then converted into the hydrochloride using 1 equivalent of 0.1 N aqueous hydrochloric acid [TLC: acetonitrile/water/glacial acetic acid 5:1:0.2 R$_f$=0.36] [FAB-MS: m/e=896 (M+H$^+$)].

Example 3

20(S)-20-O-{N$^\alpha$-[O-(3-O-Methyl-β-L-fucopyranosyl)-4-hydroxy-phenylamino-thiocarbonyl]-D-lysyl-D-leucyl}-camptothecin, hydrochloride

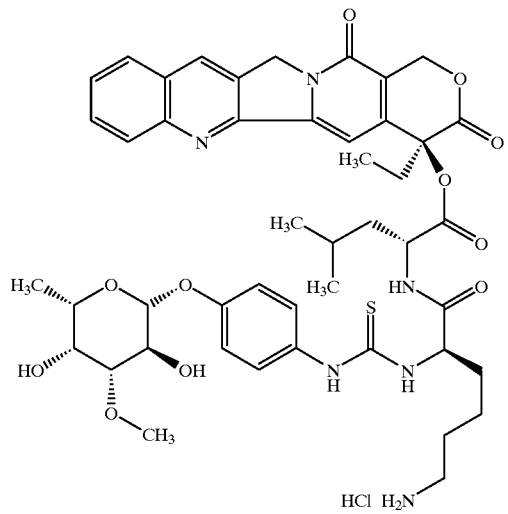

The synthesis is carried out completely analogously to Example 1. The starting materials I and IV.D are used as starting compounds here, the polar diastereomer II.b) D being employed from the 20-O-leucyl-camptothecin II.b stage. [TLC: acetonitrile/water/glacial acetic acid 5:1:0.2 R$_f$=0.31] [FAB-MS: m/e=901 M+H$^+$].

Example 4

20(S)-20-O-{N$^\alpha$-[O-(3-O-Methyl-β-L-fucopyranosyl)-4-hydroxy-phenylamino-thiocarbonyl]-L-ornithyl-D-leucyl}-camptothecin, hydrochloride

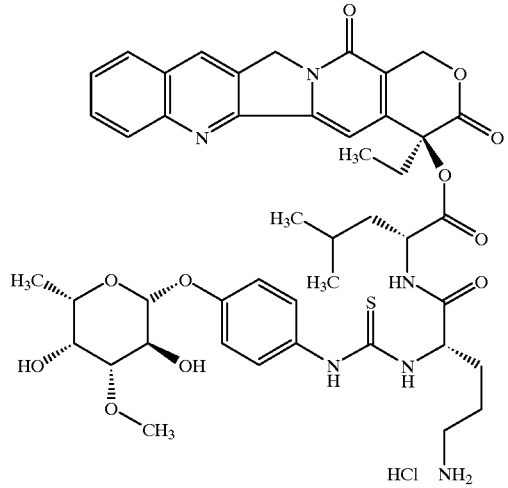

The synthesis is carried out completely analogously to Example 1. The starting materials I and V) D are used as starting compounds here, the polar diastereomer II.b) D having the D-leu configuration being employed from the 20-O-leucyl-camptothecin II.b stage. [TLC: acetonitrile/water/glacial acetic acid 5:1:0.2 $R_f$=0.25].

Example 5

20(S)-20-O-{$N^\alpha$-[O-(3-O-Methyl-β-L-fucopyranosyl)-4-hydroxy-phenylamino-thiocarbonyl]-L-arginyl-D-leucyl}-camptothecin

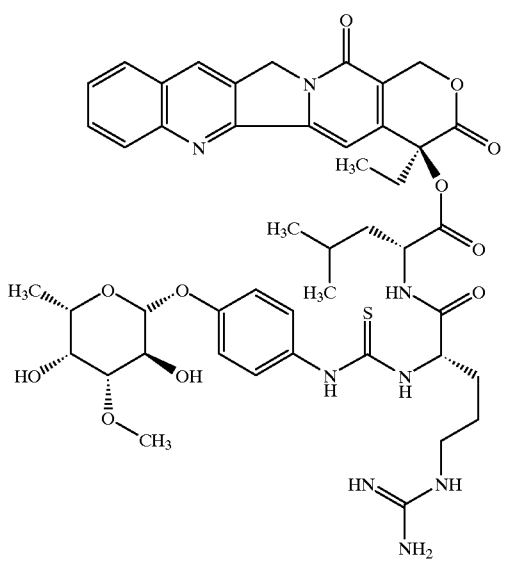

A solution of 73 mg (0.27 mmol) of p-aminophenyl-3-O-methyl-β-L-fucopyranoside (starting material I) in 20 ml of dioxane/water 1:1 is treated with stirring with 30 µl of thiophosgene (1.4 eq.). After 10 min, the mixture is treated with 4 equivalents of ethyldiisopropylamine, then concentrated in vacuo and the residue is dried for 1 h in an oil pump vacuum. The isothiocyanate obtained is dissolved in 20 ml of absolute dimethylformamide and treated with 175 mg (0.18 mmol) of compound VI) D and 620 µl of ethyldiisopropylamine. For the synthesis of compound VI) D, the polar diastereomer II.b) D is employed here from the 20-O-leucyl-camptothecin II.b stage. The mixture is stirred at room temperature for 16 h, then concentrated in vacuo and stirred with dichloromethane. The residue is then reprecipitated from dichloromethane/methanol using diethyl ether and washed with diethyl ether. It is then lyophilized from dioxane/water and then crystallized again from dichloromethane/methanol using diethyl ether. 154 mg (90%) of the target product are obtained [TLC: acetonitrile/water/glacial acetic acid 5:1:0.2 $R_f$=0.39] [FAB-MS: m/e= 929 M+H$^+$].

Example 6

20(S)-20-O-{$N^\alpha$-[O-(3-O-Methyl-β-L-fuopyranosyl)-4-hydroxy-phenylamino-thiocarbonyl]-L-lysyl-D-leucyl}-camptothecin, hydrochloride

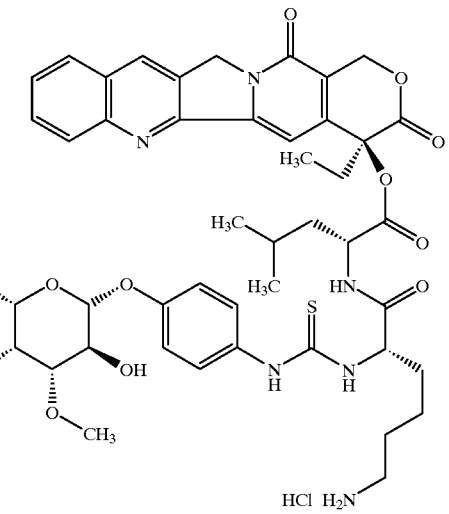

The compound is prepared in analogy to Example 1, the polar diastereomer II.b) D with the D-leucine configuration being employed in the 20-O-leucyl-camptothecin II.b stage.

Alternatively, the compound from Example 1, for example, can also be separated into the individual isomeric forms by preparative HPLC.

Conditions:

Separating column: Macherey & Nagel 250×21 mm Nucleosil 100-7 C18 AB

| | |
|---|---|
| Eluent A: | H$_2$O + 0.1M KH$_2$PO$_4$ |
| Eluent B: | Acetonitrile/water 4:1 + 0.02M KH$_2$PO$_4$ |
| flow rate: | 0 ml/min |
| Inj. volume: | 1500 µl |
| Gradient | 0–30% B |
| | 4–30 |
| | 20–90 |
| | 22–90 |
| | 24–30 |
| Wavelength: | 215 nm |

After the HPLC separation, the corresponding fractions are lyophilized and the residue is then precipitated several times from dichloromethane/methanol using diethyl ether. The mixture is then adjusted to pH 8–9, and the residue is filtered off and converted into the hydrochloride using 0.1N hydrochloric acid.

In the $^1$H-NMR spectrum, the isomers in Examples 6 and 7 show different chemical shifts, in particular for the two singlets of the aromatic H atoms in the camptothecin B ring or D ring.

Diastereomer with D-leucine

400-MHz-$^1$H-NMR (CD$_2$Cl$_2$/CD$_3$OD 1:1): δ s C—H (B ring) 8.52 ppm s C—H (D ring) 7.42 ppm

[FAB-MS: m/e=901=M+H$^+$]

Example 7

20(S)-20-O-{N$^\alpha$-O-(3-O-Methyl-β-L-fucopyranosyl)-4-hydroxy-phenylamino-thiocarbonyl]-L-lysyl-L-leucyl}-camptothecin, hydrochloride

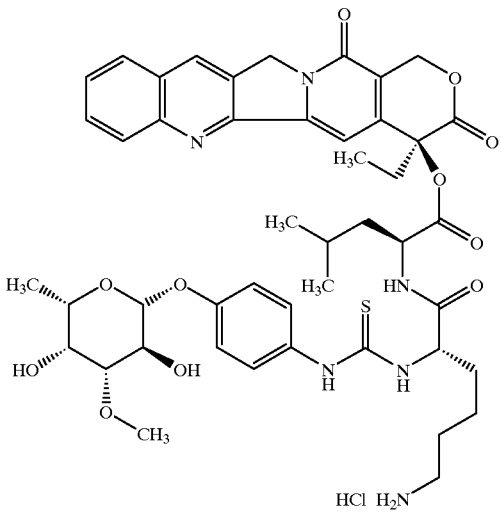

The compound is prepared in analogy to Example 1, the non-polar diastereomer II.b) L with the L-configuration of leucine being employed in the 20-O-leucyl-camptothecin II.b stage.

Alternatively, the compound from Example 1, for example, can also be separated into the individual isomeric forms by preparative HPLC.

Conditions: As Given in Example 6

After the HPLC separation, the corresponding fractions are lyophilized and the residue is then precipitated several times from dichloromethane/methanol using diethyl ether. The mixture is then adjusted to pH 8–9, and the residue is filtered off and converted into the hydrochloride using 0.1N hydrochloric acid.

In the $^1$H-NMR spectrum, the isomers in Examples 6 and 7 show different chemical shifts, in particular, for example, for the two singlets of the aromatic H atoms in the camptothecin B ring or D ring.

Diastereomer with L-leucine

400-MHz-$^1$H-NMR (CD$_2$Cl$_2$/CD$_3$OD 1:1): δ s C—H (B ring) 8.6 ppm
s C—H (D ring) 7.35 ppm
[FAB-MS: m/e=901=M+H$^+$]

Example 8

20(S)-20-O-{N$^\alpha$-[-(3-O-Methyl-β-L-fucopyranosyl)-4-hydroxy-phenylamino-thiocarbonyl]-L-lysyl-L-valyl}-camptothecin, hydrochloride

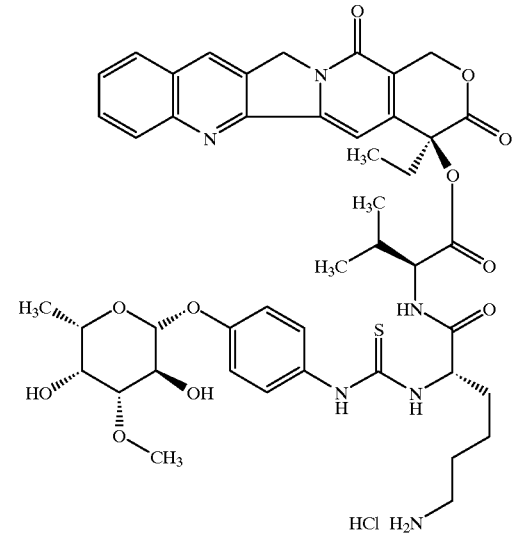

The compound is prepared in analogy to Example 1 in the non-polar series starting from the compound VII) L.

The diastereomer ratio can be determined by analytical HPLC. If appropriate, a further purification of the diastereomer with the L-configuration of valine can be achieved by crystallization from methanol (>20:1).

HPLC Conditions:
Separating column: Macherey & Nagel 250×4 mm Nucleosil 100-7 C18 AB
Eluent A: H$_2$O+0.1M KH$_2$PO$_4$
Eluent B: Acetonitrile/water 4:1+0.02M KH$_2$PO$_4$
flow rate: 1 ml/min
Inj. volume: 15 µl In the $^1$H-NMR spectrum, the pure diastereomer shows only one signal set, for example, for the two singlets of the aromatic H atoms in the camptothecin B ring or D ring.

400-MHz-$^1$H-NMR (CD$_2$Cl$_2$/CD$_3$OD 1:1): δ s C—H (B ring) 8.55 ppm
s C—H (D ring) 7.35 ppm
[FAB-MS: m/e=887=M+H$^+$]

An alternative procedure in the synthesis of the compound from Example 8 is likewise possible. In this procedure, the carbohydrate unit from Example 1 is first linked to a side chain-protected lysine derivative:

8a) N$^\alpha$-[-(3-O-Methyl-β-L-fucopyranosyl)-4-hydroxy-phenylamino-thiocarbonyl]-N$^\epsilon$-[fluorenyl-9-methoxycarbonyl]-L-lysine:

A solution of 6.8 g (25.3 mmol) of p-aminophenyl-3-O-methyl-β-L-fucopyranoside (Example I) in 600 ml of dioxane/water 1:1 is treated with stirring with 2.72 ml of thiophosgene (1.4 eq.). After 10 min, it is treated with 26 ml of ethyldiisopropylamine, stirred at RT for a further 5 min and then concentrated in vacuo to a volume of 150 ml. 800 ml of dichloromethane are added and the phases are separated. The organic phase is washed twice with water, dried over sodium sulphate and concentrated. The residue is stirred with 200 ml of methyl tert-butyl ether and 200 ml of petroleum ether and filtered off with suction. 7.26 g (92%) of the isothiocyanate are obtained.

2.92 g (9.4 mmol) of the isothiocyanate obtained are dissolved in 200 ml of dioxane/water 1:1 and treated with 3.11 g (0.9 eq.) of $N^\epsilon$-[fluorenyl-9-methoxycarbonyl]-lysine and 3.2 ml of ethyl-diisopropylamine. The mixture is stirred at room temperature for 16 h, then concentrated in vacuo and the residue is taken up with water. By adjusting the pH to 2 with 1N HCl, the product is precipitated and filtered off with suction after 30 min. The residue is suspended in dichtoromethane and the solvent is stripped off twice. After washing with ether and petroleum ether several times, 5.3 g (92%) of target product are obtained [TLC: acetonitrile/water/glacial acetic acid 5:1:0.2 $R_f$=0.69].

8b) 20(S)-20-O-{$N^\alpha$-[O-(3-O-Methyl-β-L-fucopyranosyl)-4-hydroxy-phenylamino-thiocarbonyl]-$N^\epsilon$-[fluorenyl-9-methoxycarbonyl]-L-lysyl-L-valyl}-camptothecin:

1.2 g (1.76 mmol) of $N^\alpha$-[O-(3-O-methyl-β-L-fucopyranosyl)-4-hydroxy-phenylamino-thiocarbonyl]-$N^\epsilon$-[fluorenyl-9-methoxycarbonyl]-L-tysine (Example 8a) and 675 mg (1.2 mmol) of the compound III.b) L are dissolved in 50 ml of dimethylformamide, and the mixture is cooled to 0° C. and then treated with 346 mg (1.8 mmol) of N-ethyl-N'-(dimethylaminopropyl)-carbodiimide hydrochloride. The temperature is allowed to rise to RT overnight with stirring. The solvent is evaporated in vacuo and the residue is stirred with water. It is purified by flash chromatography on silica gel, starting with acetonitrile as eluent and later changing to acetonitrile/water 50:1. After concentrating the corresponding fractions, 1.06 g (76%) of the target product are obtained [TLC: acetonitrile/water 20:1 $R_f$=0.34].

The deblocking and the subsequent conversion into the hydrochloride is carried out in analogy to Example 1.

Example 9

20(S)-20-O-{$N^\alpha$-[O-(3-O-Methyl-β-L-fucopyranosyl)-4-hydroxy-phenylamino-thiocarbonyl]-L-histidyl-L-valyl}-camptothecin, hydrochloride

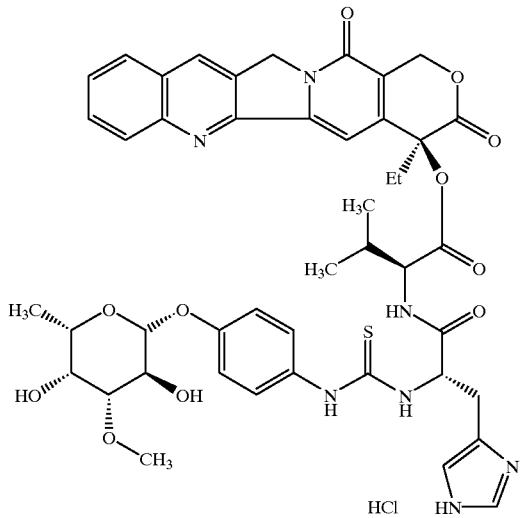

Starting from the non-polar diastereomer of 20-O-valyl-camptothecin, trifluoroacetate (III.b) L, the compound is prepared in analogy to Example 2. The diastereomer ratio can be determined by analytical HPLC. If appropriate, a further purification of the non-polar diastereomer having the L-configuration of valine can be achieved by crystallization from methanol (>20:1)

HPLC conditions:

Separating column: Macherey & Nagel 250×4 mm Nucleosil 100-7 C18 AB

Eluent A: $H_2O$+0.1M $KH_2PO_4$

Eluent B: Acetonitrile/water 4:1+0.02M $KH_2PO_4$ flow rate: 1 ml/min

Inj. volume: 15 µl

In the $^1$H-NMR spectrum, the pure diastereomer shows only one signal set, e.g. for the two singlets of the aromatic H atoms in the camptothecin B ring or D ring.

Diastereomer with L-valine:

400-MHz-$^1$H-NMR ($CD_2Cl_2$/$CD_3OD$ 1:1): δ s C—H (B ring) 8.58 ppm (overlaid by a CH arom. of histidine) s C—H (D ring) 7.35 ppm

[TLC: acetonitrile/water/glacial acetic acid 5:1:0.2 $R_f$=0.36[[FAB-MS: m/e=896 (M+H$^+$)].

Example 10

20(S)-20-O-{$N^\alpha$-[O-(3-O-Methyl-β-L-fucopyranosyl)-4-hydrdxy-phenylamino-thiocarbonyl]-L-arginyl-L-leucyl}-camptothecin

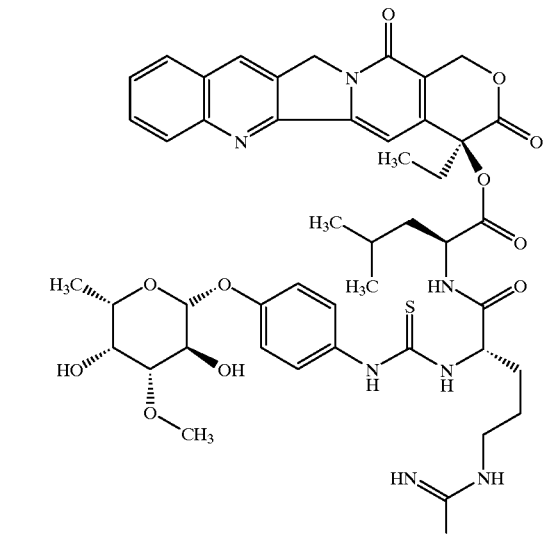

The product is prepared in analogy to Example 5. The non-polar diastereomer II.b) L is employed here in the 20-O-leucyl-camptothecin II.b) stage. [TLC: acetonitrile/water/glacial acetic acid 5:1:0.2 $R_f$=0.4[[FAB-MS: m/e= 929=M+H$^+$].

Using the HPLC conditions given under Examples 8 and 9, the diastereomers from Examples 5 and 10 can be differentiated.

What is claimed is:

1. A camptothecin glycoconjugate of formula (I)

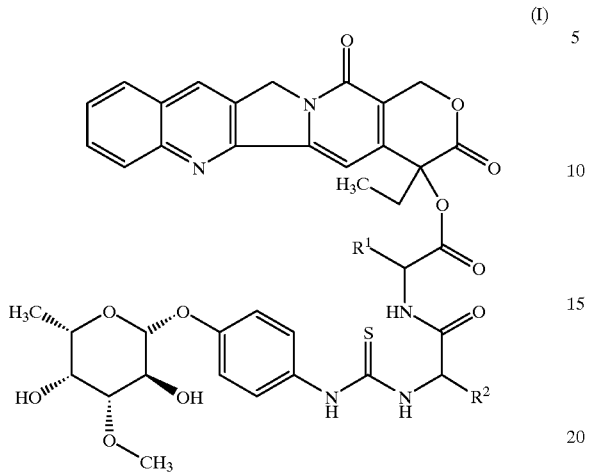

(I)

in which

R$^1$ represents a β- or γ-branching non-polar amino acid side chain; and

R$^2$ represents a basic amino acid side chain;

and their salts, stereoisomers and stereoisomer mixtures.

2. The compound of formula (I) according to claim 1, where

R$^1$ is a branched alkyl radical having up to 4 carbon atoms; and

R$^2$ is a radical of the formula —(CH$_2$)$_n$—R$^3$, where

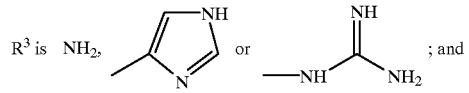

n is a number 1 to 4;

and their salts, stereoisomers and stereoisomer mixtures.

3. The compound of the formula (I) according to claim 1, where

R$^1$ is a branched alkyl radical of formula

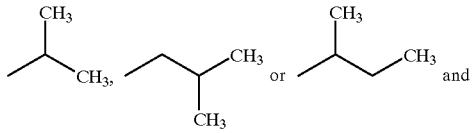

R$^2$ is a radical of the formula

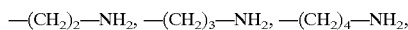

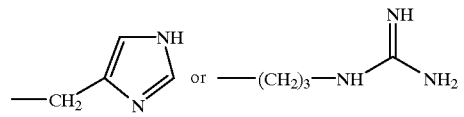

and their salts, stereoisomers and stereoisomer mixtures.

4. A process for the preparation of a glycoconjugate of formula (I)

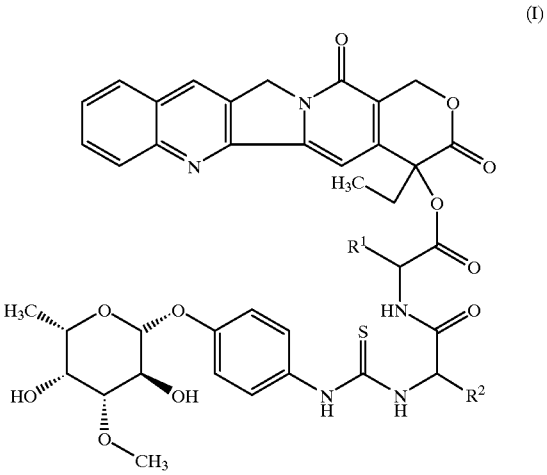

(I)

in which

R$^1$ represents a β- or γ-branching non-polar amino acid side chain; and

R$^2$ represents a basic amino acid side chain, or of their salts, wherein the isothiocyanate of the formula (II)

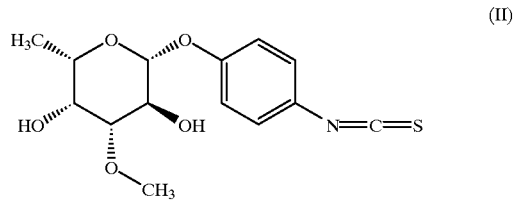

(II)

is reacted with the peptidyl-camptothecin, optionally bearing a protective group in the side chain, of the formula (III)

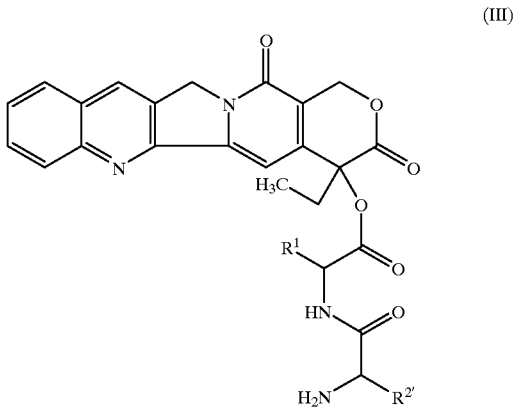

(III)

in which

R$^1$ has the abovementioned meaning and

R$^{2'}$ has the meaning of the abovementioned basic radical R$^2$, which moreover can carry a protective group on the basic group to give the glycoconjugate of the formula (IV)

(IV)

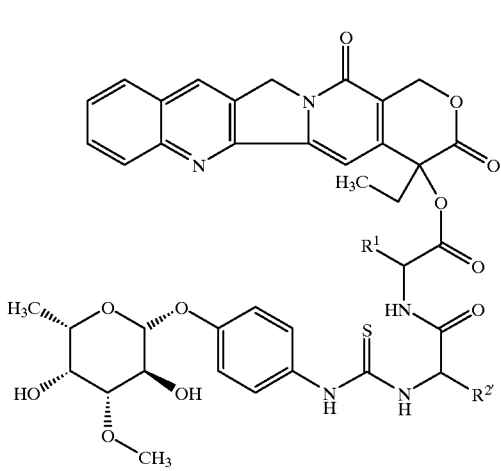

in which
R¹ and R²' have the meanings indicated above,
wherein the side chain amino protective group which may be present is optionally removed and the compound obtained is optionally converted into the desired salt.

5. A process for the preparation of compounds of the general formula (I) or of their salts, characterized in that the isothiocyanate of formula (II)

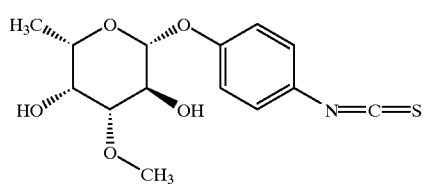

is reacted with an optionally protected terminal basic amino acid of the formula (V)

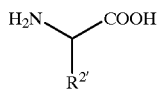

in which R²' represents a basic amino acid side chain whose basic group can be protected,
to give an amino acid conjugate of the formula (VI)

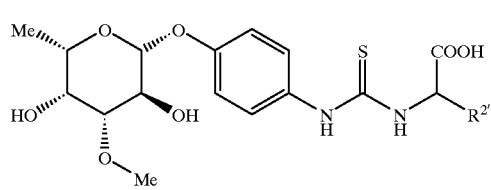

in which R²' has the meaning indicated above,
this is then reacted with amino acid conjugates of the formula (VII)

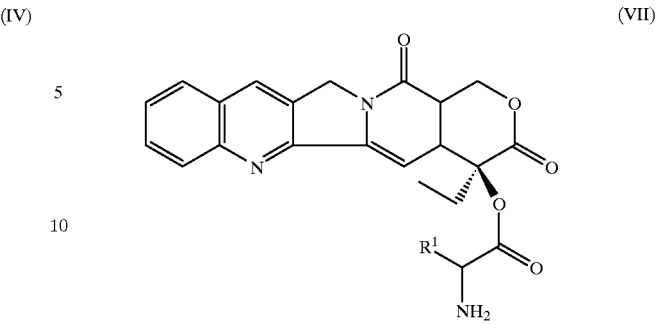

in which R¹ has the meaning indicated in claim 1,
wherein the side chain protective group is optionally removed and the compounds are optionally converted into a suitable salt.

6. The compound 20(S)-20-O-{N^α-[O-(3-O-methyl-β-L-fucopyranosyl)-4-hydroxy-phenylamino-thiocarbonyl]-L-lysyl-L-valyl}-camptothecin of the formula

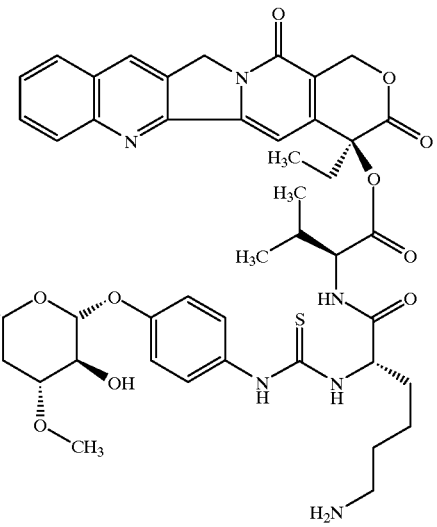

and its salts.

7. The compound 20(S)-20-O-{N^α-[O-(3-O-methyl-β-L-fucopyranosyl)-4-hydroxy-phenylamino-thiocarbonyl]-L-histidyl-L-valyl}-camptothecin of the formula

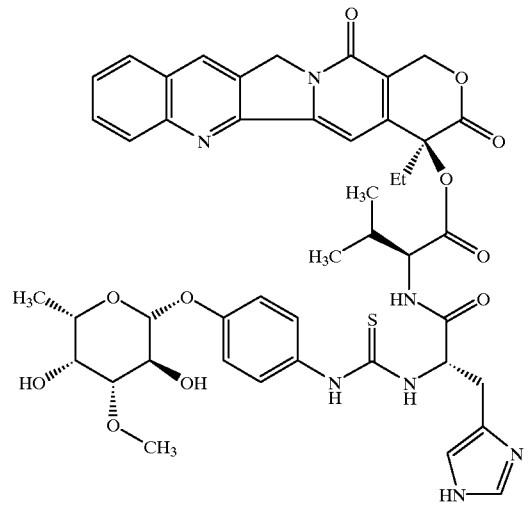

and its salts.

8. A pharmaceutical composition comprising a compound according to claim 1 and a pharmaceutically acceptable carrier.

9. A method for the treatment of oncoses, comprising administering to a mammal in need thereof an effective amount of a compound according to claim 1.

10. The method of claim 9, wherein said mammal is a human.

11. A method of inhibiting tumor growth in a mammal, comprising administering an effective amount of a compound according to claim 1 to said mammal.

12. The method of claim 11, wherein said mammal is a human.

* * * * *